United States Patent [19]
Beck

[11] Patent Number: 6,129,698
[45] Date of Patent: Oct. 10, 2000

[54] CATHETER

[76] Inventor: Robert C Beck, 2256 Hendon Ave., St. Paul, Minn. 55108

[21] Appl. No.: 08/862,277

[22] Filed: May 23, 1997

Related U.S. Application Data

[60] Provisional application No. 60/018,333, May 24, 1996.

[51] Int. Cl.[7] .................................................. A61M 1/00
[52] U.S. Cl. ............................................. 604/27; 604/30
[58] Field of Search ..................... 604/22, 35, 19, 604/20, 21, 27, 39, 40, 43, 246, 247, 264, 523; 606/159, 167, 170, 179, 180

[56] References Cited

U.S. PATENT DOCUMENTS

| | | | |
|---|---|---|---|
| 4,681,106 | 7/1987 | Kensey et al. | 128/305 |
| 4,808,153 | 2/1989 | Parisi . | |
| 5,114,399 | 5/1992 | Kolvacheck | 604/22 |
| 5,195,956 | 3/1993 | Stockmeier | 604/22 |
| 5,224,945 | 7/1993 | Pannek, Jr. | 606/159 |
| 5,273,526 | 12/1993 | Dance et al. | 604/35 |
| 5,284,473 | 2/1994 | Calabria . | |
| 5,318,576 | 6/1994 | Plassche, Jr. et al. | 606/159 |
| 5,344,395 | 9/1994 | Whalen . | |
| 5,540,707 | 7/1996 | Ressemann et al. | 606/159 |
| 5,846,219 | 12/1998 | Vancaillie . | |

FOREIGN PATENT DOCUMENTS 1002274  2/1996  Netherlands .

OTHER PUBLICATIONS

"Reba, I." Applications of the Coaneda Effect, Scientific American, Jun. 1966 pp. 84–92.
"Walker, J." The Amateur Scientist Scientific American Jun. 1966, pp. 143–150.

*Primary Examiner*—John D. Yasko
*Assistant Examiner*—Manuel Mendez
*Attorney, Agent, or Firm*—Beck & Tysver P.L.L.C.

[57] ABSTRACT

A hydraulic catheter which uses a deflected jet to entrain thrombus into a discharge lumen. Multiple energy sources including ultra sonic mechanical and optical energy may be used with the deflected jet energy.

16 Claims, 4 Drawing Sheets

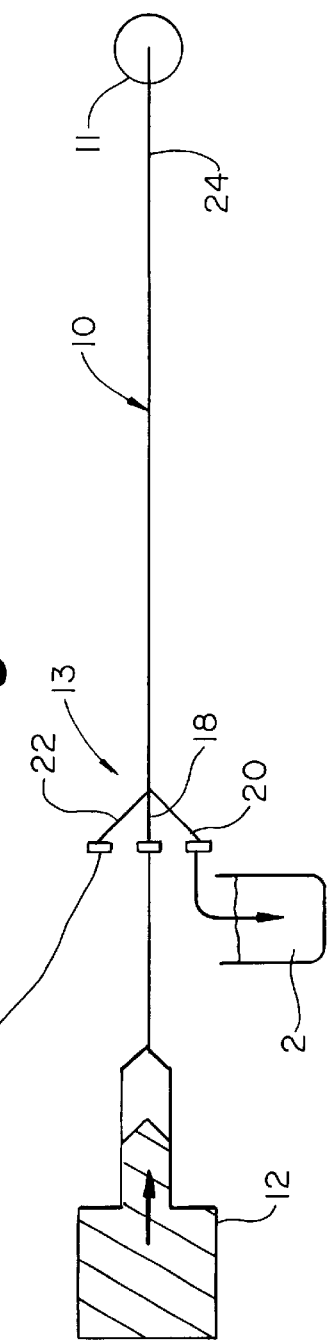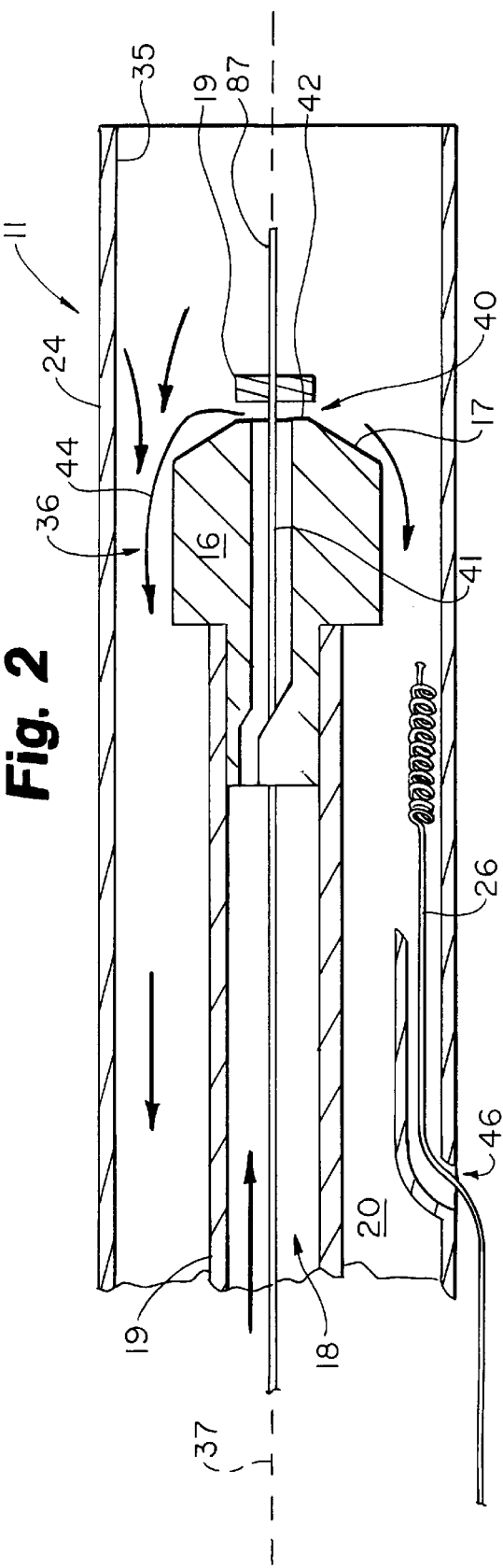

CATHETER

CROSS REFERENCE TO RELATED APPLICATIONS

The present application claims the benefit of provisional patent application Ser. No. 60/018,333 filed May 24, 1996 entitled "Thrombectomy Catheters".

1. FIELD OF THE INVENTION

The invention relates generally to a catheter, and more particularly to a device that utilizes the energy in a pressurized fluid to interact with and remove occlusive material from vessels or lumens in the body.

2. BACKGROUND OF THE INVENTION

Catheters which are used to remove occlusive material from lumens within the body are well known. Occlusive material such as plaque, atheroma, and emboli vary in their mechanical properties and various energy sources have been proposed to break up occlusive material. These proposals include the use of high energy fluid jets or the circulation of an abrasive slurry within the vessel. The use of mechanical impellers and/or blades has been proposed and experimental work has been performed with a "rotoblader" device. Laser light energy and either ultrasonic or acoustic energy have been proposed to breakdown occlusive material. The use of radio frequency electromagnetic energy has been proposed as well. For example fluid pressure thrombectomy systems are known from U.S. Pat. No. 4,690,672 to Veltrup among others. In the Veltrup device, a reward-facing jet entrains thrombus and blood from the patient, and ejects these into a secondary discharge lumen which removes both thrombus and blood from the body. Linear or straight line fluid jets which represent the current technology, are relatively inefficient in removing thrombus because of the jet geometry.

Impeller based cutting devices are known from U.S. Pat. No. 4,729,763 among others. In this device the mechanically rotated blade interacts directly with the occlusive material.

Ultrasonic based devices are known from U.S. Pat. No. 5,368,557. In this device the ultrasonic energy is used to break up the occlusive material and a fluid is supplied to cool the ultrasonic tip. In general there are two functions which must be supplied. First sufficient energy must be available to disrupt the occlusive material. Secondly loose material must be efficiently removed from the body. Most particulate occlusive material is thrombogenic and failure to remove this material can result in a distal embolism.

SUMMARY OF THE INVENTION

In contrast to the devices of the prior art, the present invention teaches the use of a deflected jet alone or in conjunction with a complimentary energy source to break up and transport occlusive material out of the body. The deflected jet is a substantially annular sheet of fluid which becomes attached to a barrier and which is then deflected through an angle. This deflected jet entrains ambient fluid on its outer surface and the combined stream is deflected through an angle of about ninety degrees in most embodiments. This deflected jet presents a large and energetic surface to entrain and emulsify occlusive material. In operation the jet emerges from a generally annular nozzle or slit and attaches itself to a shoulder of a flow control body. As the jet emerges from the nozzle it spreads over the contour of the shoulder which gives the jet a greater working area. The jet ultimately enters a throat formed in the catheter which provides good pressure recovery for the jet improving overall efficiency.

In some versions, the catheter may be delivered over a guide wire or through a guide sheath. The construction and geometry of the device permits integration with other energy sources. In these alternate embodiments the deflected jet acts a pump to emulsify and preferentially remove particulate occlusive material. Examples of disclosed energy sources include mechanical impellers, ultrasonic probes, radio frequency probes, and laser fiber systems.

BRIEF DESCRIPTION OF THE DRAWING

The drawings show illustrative embodiments of the catheter. Various modifications to these designs may be made without departing from the scope of the invention. Elements which carry identical reference numerals are equivalent structures.

FIG. 1 is a system level diagram, showing a simple version of the catheter system;

FIG. 2 is a schematic diagram of the distal end of the catheter;

DETAILED DESCRIPTION

Figure 3:
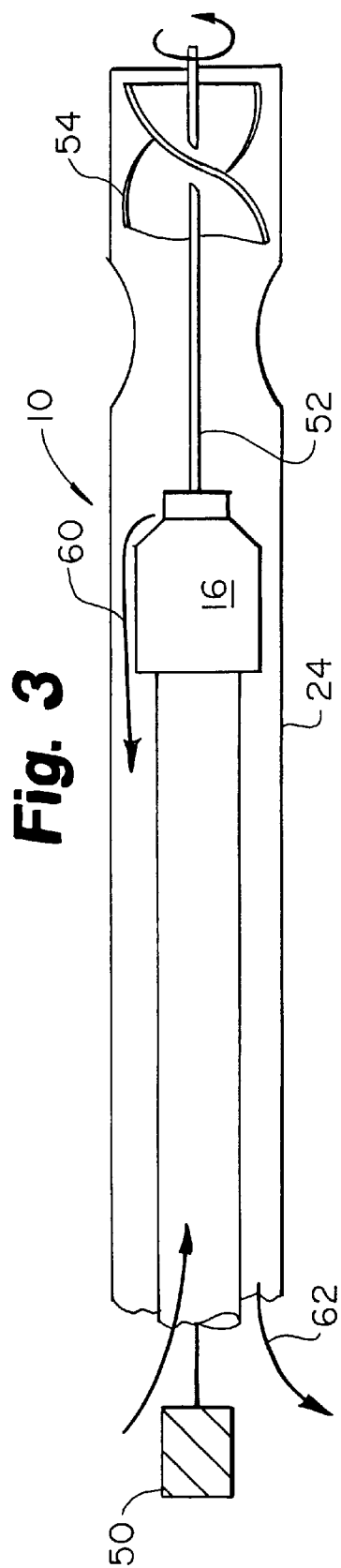
FIG. 3 is a schematic diagram of an alternate embodiment of the catheter.

Turning to FIG. 1, the catheter assembly 10 is coupled to an angiographic fluid injector 12. The catheter assembly 10 has a distal end 11 and a proximal end 13. The proximal end includes fittings for a high pressure supply lumen 18 and a lower pressure discharge lumen 20 and a guide wire lumen 22. In the figure the high pressure injector 12 supplies saline from a saline supply at a user selected delivery rate which generates a corresponding pressure sufficient to induce the required flow. Typically, an over-pressure switch is present on the injector 12 to shut the injector off if the high pressure supply line pressure exceeds a pre-set value. In use, the distal end 11 of the catheter assembly 10 interacts with the thrombus or other occlusive material and the energetic saline fluid jet entrains both blood and thrombus from the patient, which are discharged through the lower pressure discharge lumen 20 to a collection vessel 2. In the preferred use, the catheter 10 is delivered by the guide wire 26 to an occluded site in the vasculature. The injector 12 is then activated and the occlusive material is extracted by the deflected jet into the collection vessel 2.

FIG. 2, shows the distal 11 end portion of an illustrative embodiment of the catheter assembly 10 in cross section. The outer diameter of the catheter assembly 10 is defined by the sheath 24. The interior lumen of this sheath 24 forms and defines one wall 35 of a throat 36 formed between the wall 35 and the outer diameter of the flow control body 16. The sheath 24 also defines a central axis 37 for the distal portion 11 of the assembly. The high pressure supply tubing 19 has a lumen 18 which is used to deliver fluid to a slit 40. The slit 40 discharges fluid in a generally radial direction with respect to the central axis 37. In operation, the slit 40 will have dimensions defining an orifice area smaller than the cross-sectional dimension of the interior of the high pressure supply lumen 18. In the figure the slit 40 directs the jet away from the central axis at ninety degrees but other angles are contemplated within the scope of the disclosure. A small land area 42 may be formed on the flow control body 16. This land area 42 helps to turn the sheet of fluid 44 which emerges from the slit 40. As the fluid emerges, it entrains fluid on both sides of the jet. Since the amount of fluid which can be entrained on the inner side next to the flow control body 16 is limited, the jet turns and follows the contour of the body 16, thus turning through approximately ninety degrees in the illustrative example into the annular throat 36 formed between the sheath 24 and the body 16. Both lesser and greater degrees of turning are contemplated at least between 45 and 270 degrees. Ninety degrees of turning is desirable because it presents more fluid entrainment area to engage and eject thrombus. The non-symmetrical jet is highly turbulent and has many eddies. As a consequence the average velocity in the outer surface of the jet is higher than the average flow over the attachment wall 17 of the flow control body 16. Therefore the jet velocity is higher than a conventional jet at the same distance.

This embodiment of the device also shows a guide wire 26 which may be used to position the sheath 24 within a body vessel. For use in coronary applications, it is important that the guide wire be small, and the sheath 24 is shown with an opening 46 which permits the sheath 24 to be delivered over the guide wire 26. It should also be noted, that the position of the aperture 46 is sufficiently proximal of the distal end of the sheath 24 to permit retraction of the guide wire 26 fully into the discharge lumen 20. As seen in the figure there is a strut 41 which anchors the cap 19 into the flow control body 16. This strut 41 may extend beyond the cap 19 toward the open distal end of the sheath 24. If appropriately formed this portion of the strut may serve as a fixed guide wire and extend as shown by dotted line in the figure. Thus the flow body 16 may have a guide wire element or the sheath 24 may be advanced over a guide wire 26. As seen in the figure the strut can extend toward the proximal end of the catheter and serve as a fixed guide wire 87.

In the embodiment shown in FIG. 2 it is possible to move the flow control body 16 with respect to the sheath. When a small (3F) flow body is used, the sheath and flow body 16 may be advanced sequentially. The high pressure tubing 19 may be made of hypo tubing or more preferably polyimide tubing. When metal hypo tubing is used the flow body and tubing have the mechanical properties of a guide wire and may be used instead of a guide wire to position the flow body. If polyimide tubing is used the injector can be used to provide low pressure fluid to stiffen the tubing 19 permitting it to be used as a guide wire as well. It should also be noted that the cap 19 may be positioned off center to provide a flow body which advances and turns as it is activated outside the sheath 24. When viewed under imaging equipment this version of the device is steerable under physician control.

FIG. 3 shows an illustrative alternate second embodiment or design for the catheter assembly 10. In this version of the device an additional energy source is provided. For example an air motor 50 is coupled by a flexible shaft 52 to a distal impeller 54. In operation the impeller is rotated inducting thrombus or other occlusive material into the sheath 24. The masticated material accumulates near the flow control body 16 and the deflected jet 60 entrains this material and ejects it from the device as indicated by stream 62. In this fashion a mechanical blade or impeller can supplement the action of the deflected jet to treat patients with more organized occlusive material.

Figure 4:
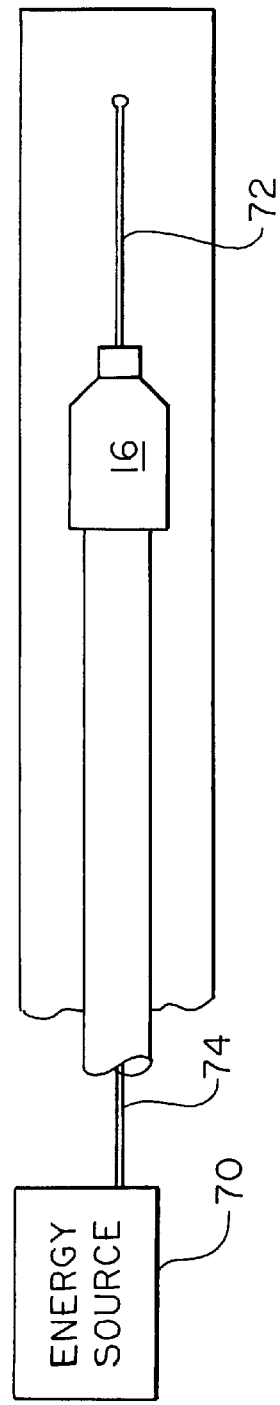
FIG. 4 is a schematic diagram of an alternate embodiment of the catheter.

FIG. 4 shows a remote energy source 70. Several different sources are represented generically by block 70. Specifically included are sources for laser light energy, ultrasonic acoustic energy, and radio frequency electromagnetic energy. In the case of ultrasonic energy and radio frequency energy the probe section may be metal. If the energy source is laser light the probe 72 may be an optical fiber with a lens or other distribution optic at the distal tip of the probe 72. In general the probe which extends distal of the flow control body 16 is connected to the energy source 70 through a suitable conduit 74.

Figure 5:
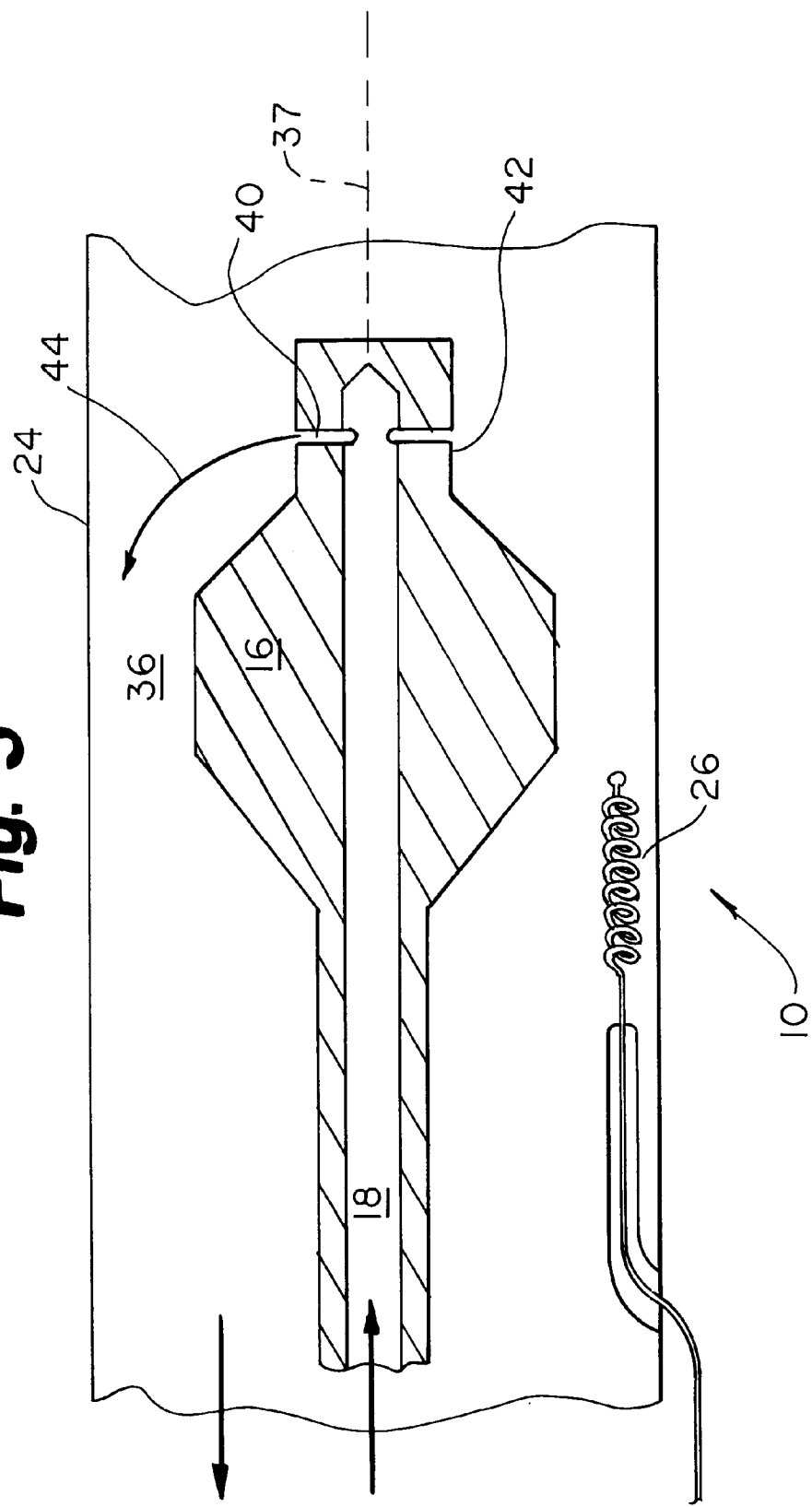
FIG. 5 is a schematic diagram of an alternate embodiment of the catheter.

Turning to FIG. 5, there is shown a distal 11 end portion of an illustrative first embodiment of the thrombectomy catheter 10. The outer diameter of the thrombectomy catheter 10 is defined in this embodiment by the sheath 24 which also forms and defines one wall of a throat 36 with respect to a flow control body 16. The sheath 24 also defines a central axis 37. The high pressure supply lumen 18 delivers fluid to a slit 40 which discharges fluid in a generally radial direction with respect to the central axis 37. In operation, the slit 40 will have dimensions defining a slit orifice area smaller than the cross-sectional dimension of the interior of the high pressure supply lumen 18. In the figure the slit 40 directs the jet away from the central axis at ninety degrees but other angles are contemplated within the scope of the disclosure. A slight step 42 may be formed proximate the flow control body 16. The height of the step helps to turn the sheet of fluid 44 which emerges from the slit 40. As the fluid emerges, it entrained fluid on both sides of the jet. Since the amount of fluid which can be entrained on the inner side next to the flow control body 16 is limited, the jet turns and follows the contour of the body 16, thus turning through approximately ninety degrees in the illustrative example into the annular throat 36 formed between the sheath 24 and the body 16. Both lesser and greater degrees of turning are contemplated. Ninety degrees of turning is desirable because it presents more fluid entrainment area to engage and eject thrombus.

This embodiment of the device also shows a guide wire 26 which may be used to position the thrombectomy catheter 10 within a body vessel. For use in coronary applications, it is important that the guide wire be small, and the discharge sheath is shown with an opening 46 which permits the thrombectomy device 10 to be delivered over the guidewire 26. It should also be noted, that the position of the aperture 46 is sufficiently proximal of the distal end of the sheath 24 to permit retraction of the guide 26 fully into the discharge lumen 20.

Figure 6:
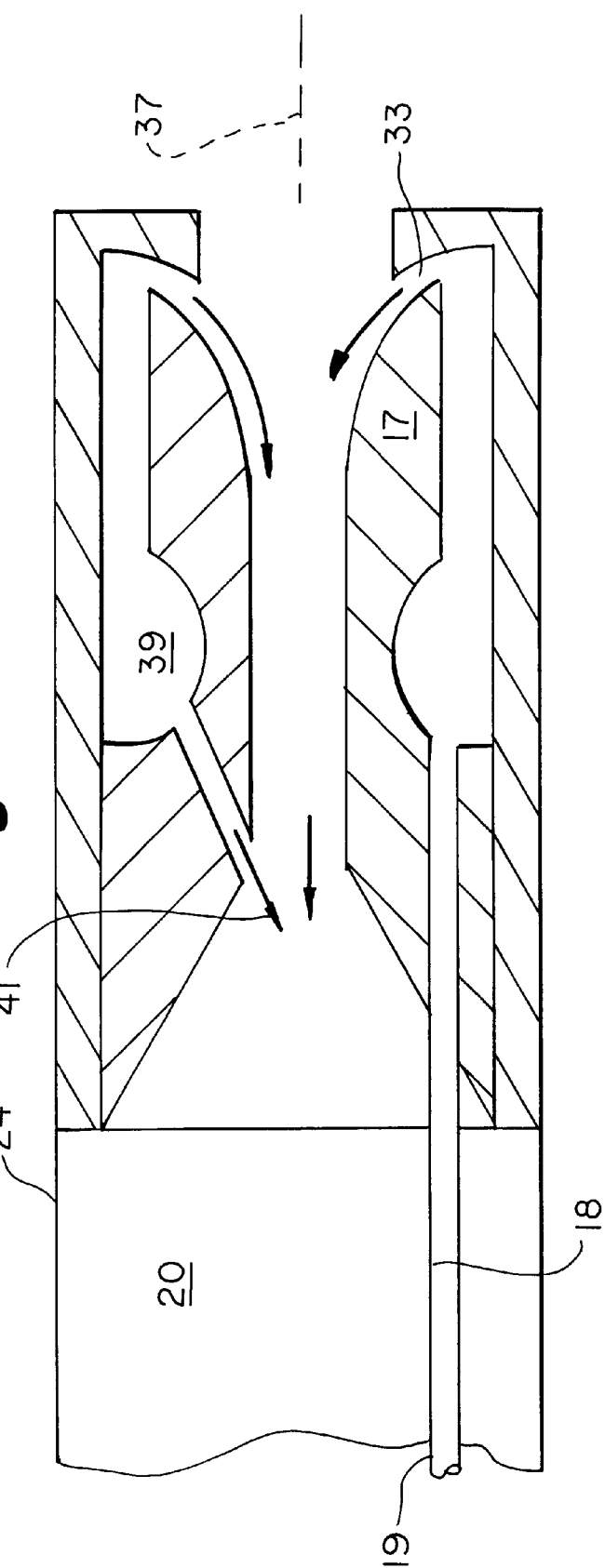
FIG. 6 is a schematic diagram of an alternate embodiment of the catheter.

FIG. 6 shows an illustrative alternate second embodiment or design for the thrombectomy catheter 10. In this version of the device the nozzle slit 33 is formed as an annular ring at the periphery of the outer sheath 24. Once again the jet is issued radially at an angle with respect to the central axis 37. In this version secondary jets 41 may be formed between the supply lumen and the discharge lumen to assist in removal of debris. In this version the high pressure supply lumen 18 delivers fluid to the plenum 39 which distributes the fluid to the annular ring jet 33. The control body 17 forms a throat 35 which may be large enough to permit passage of a guide wire through the throat area. Although the slits in each embodiment differ in detail each preferably has a characteristic length which is larger than the corresponding width. However due to manufacturing considerations rows of round holes may be substituted for the slit shown in the figures. It should also be noted that the complex body contours can be approximately by more easily manufactured conical sections.

What is claimed:

1. A catheter comprising:
   a catheter body having a proximal end and a distal end;
   a first high pressure supply lumen located in said catheter body;
   said catheter body defining a central axis;
   a cap located near said distal end of said catheter body for blocking said high pressure supply lumen at the location of said cap, said cap having a first maximum diameter;
   a control body located near said cap said body having a first diameter substantially equal to said first diameter of said cap and said diameter increasing in the direction of flow to a second maximum diameter greater than the first maximum diameter of said cap;
   said high pressure supply lumen having a proximal end and having a distal end;
   a slit formed by the junction of said cap and said body, said slit communicating with said high pressure lumen proximate said distal end, said slit directing a jet of fluid in a direction away from said central axis, thereby forming a sheet jet;
   said control body positioned near said slit to turn said sheet jet through an angle with respect to said central axis generating a deflected jet.

2. The device of claim 1, further including an aperture located in said catheter body proximal of said distal end on said catheter body for receiving a guide wire.

3. A catheter comprising:
   an elongate flexible catheter body, said body defining an axis,
   a discharge lumen located in said catheter body;
   a fluid supply lumen located in said catheter body;
   said supply lumen connected to a nozzle formed by a slit communicating with said supply lumen, said slit having a land area substantially perpendicular to said axis, said nozzle having a first diameter,
   whereby said nozzle ejects a jet of fluid in a direction away from said catheter body;
   a control body having a second diameter greater than said first diameter located near said nozzle; whereby said fluid jet attaches to and follows said control body, generating a fluid flow along said control body;
   a throat communicating with said discharge lumen for receiving said fluid flow and for directing said fluid flow out of said discharge lumen.

4. A catheter for removing occlusive material from a patient comprising:
   a fluid supply lumen terminating in a nozzle said nozzle forming a fluid jet, a control body located near said nozzle said nozzle having a cap side having a first diameter and a control body side, said control body having a second diameter greater than said first diameter,
   said control body located near said jet for limiting entrainment of fluids on said control body side of said fluid jet;
   whereby said fluid jet becomes attached to said control body and follows the contour of said body;
   a discharge lumen located near said body to receive fluid from said jet.

5. A catheter having a distal end and having a proximal end, said catheter comprising:
   a high pressure lumen:
   a low pressure lumen;
   a deflected jet formed by a slit communicating with said high pressure lumen at a location adjacent a control body, said control body meeting said slit at a first location adjacent said slit and having a characteristic dimension at said first location, said control body having a larger dimension at a second location located a distance away from said slit;
   said control body located near said distal end whereby said deflected jet entrains and collects occlusive material and flows substantially retrograde toward said proximal end of said catheter body, along said control body thereby directing said occlusive material into said low-pressure lumen.

6. The device of claim 5 further including a impeller located distal of said deflected jet.

7. The device of claim 5 further including a blade located distal of said deflected jet.

8. The device of claim 5 further including a sonic probe located distal of said deflected jet.

9. The device of claim 5 further including a radio frequency energy probe located distal of said deflected jet.

10. The device of claim 5 further including an ultrasonic energy probe located distal of said deflected jet.

11. A catheter comprising:
    a catheter body, said catheter body having distal end and a proximal end, said catheter body defining a central axis along the length of said body;
    a supply lumen located within said catheter body, and coupled to a source of fluid;
    an annular aperture communicating with said supply lumen, said annular aperture located around said central axis;
    an annular control body having first dimension at a first location near said aperture and having a second dimension at a second location downstream of said aperture, said control body gradually increasing in dimension from said first location to said second location, said control body located near said annular aperture such that fluid exiting said aperture is directed radially outward with respect to said central axis and attaches to said control body and flows along said control body toward the proximal end of said catheter body;
    a discharge lumen located within said catheter body and having an annular throat proximate said aperture whereby fluid from said supply lumen discharges into said throat and is extracted from the catheter body.

12. The catheter of claim 11 wherein said supply lumen, discharge lumen and control body are symmetrically located in said catheter body about said central axis.

13. The catheter of claim 12 wherein said control body is radially symmetric about said central axis.

14. The catheter of claim 13 wherein said annular aperture discharges fluid at a discharge angle with respect to said axis of between approximate 45 degrees and 90 degrees.

15. The catheter of claim 13 wherein said annular aperture discharges fluid at a discharge angle with respect to said axis of between approximate 45 degrees and 270 degrees.

16. The device of claim 1 further including a sheath forming a low pressure lumen; said sheath adapted for relative motion with respect to said control body, whereby said control body may operate either outside or inside of said sheath.

* * * * *